(12) United States Patent
Vilos

(10) Patent No.: US 6,500,113 B2
(45) Date of Patent: *Dec. 31, 2002

(54) DEBRIS ASPIRATING RESECTOSCOPE

(76) Inventor: George A. Vilos, 14511 Sprucedale Avenue, London, Ontario (CA), N5X 2N7

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,966
(22) PCT Filed: Mar. 30, 1998
(86) PCT No.: PCT/CA98/00301
§ 371 (c)(1), (2), (4) Date: Oct. 1, 1999
(87) PCT Pub. No.: WO98/43531
PCT Pub. Date: Oct. 8, 1998

(65) Prior Publication Data
US 2002/0072651 A1 Jun. 13, 2002

(30) Foreign Application Priority Data
Apr. 1, 1997 (CA) .............................................. 2201458

(51) Int. Cl.$^7$ ................................................. A61B 1/12
(52) U.S. Cl. ........................ 600/105; 600/156; 600/158
(58) Field of Search ................................. 600/105, 128, 600/130, 153, 156, 158

(56) References Cited

U.S. PATENT DOCUMENTS

| | | | |
|---|---|---|---|
| 4,681,106 A | 7/1987 | Kensey et al. | |
| 5,000,185 A | 3/1991 | Yock | |
| 5,088,998 A | * 2/1992 | Sakashita et al. | 606/46 |
| 5,133,713 A | 7/1992 | Huang et al. | |
| 5,176,677 A | 1/1993 | Wuchinich | |
| 5,201,731 A | 4/1993 | Hakky | |
| 5,313,949 A | 5/1994 | Yock | |
| 5,314,438 A | 5/1994 | Shturman | |
| 5,325,860 A | 7/1994 | Seward et al. | |
| 5,335,663 A | 8/1994 | Oakley et al. | |
| 5,345,940 A | 9/1994 | Seward et al. | |
| 5,456,689 A | 10/1995 | Kresch et al. | |
| 5,527,331 A | 6/1996 | Kresch et al. | |
| 5,536,234 A | 7/1996 | Newman | |
| 5,540,656 A | 7/1996 | Pflueger et al. | |
| 5,540,658 A | 7/1996 | Evans et al. | |
| 5,540,678 A | 7/1996 | Long et al. | |
| 5,540,679 A | 7/1996 | Fram et al. | |
| 5,540,683 A | 7/1996 | Ichikawa et al. | |
| 5,542,917 A | 8/1996 | Nita et al. | |
| 5,542,918 A | 8/1996 | Atkinson | |
| 5,542,928 A | 8/1996 | Evans et al. | |
| 5,542,929 A | 8/1996 | Laabs et al. | |
| 5,807,240 A | * 9/1998 | Muller et al. | 600/135 |

* cited by examiner

Primary Examiner—Linda C. M. Dvorak
Assistant Examiner—Jocelyn Ram
(74) Attorney, Agent, or Firm—Bereskin & Parr

(57) ABSTRACT

A resectoscope for internal surgery generally comprising an operating handle having extendible instruments such as a cutting tool, viewing means such as a telescope and a light conduit and passageways to supply and remove aspirating fluid to lubricate and to wash the surgical site wherein said extendible instruments are contained within a tube divided in cross section by longitudinal wall into first and second sectors, said first sector being smaller than the second sector and containing the viewing means and providing a passageway for the supply of as pirating fluid, said second sector containing the cutting tool and providing a large passageway for the removal of aspirating fluid and surgical morsels for collection and optionally having a valving mechanism activated by retraction or extension of the cutting tool.

8 Claims, 2 Drawing Sheets

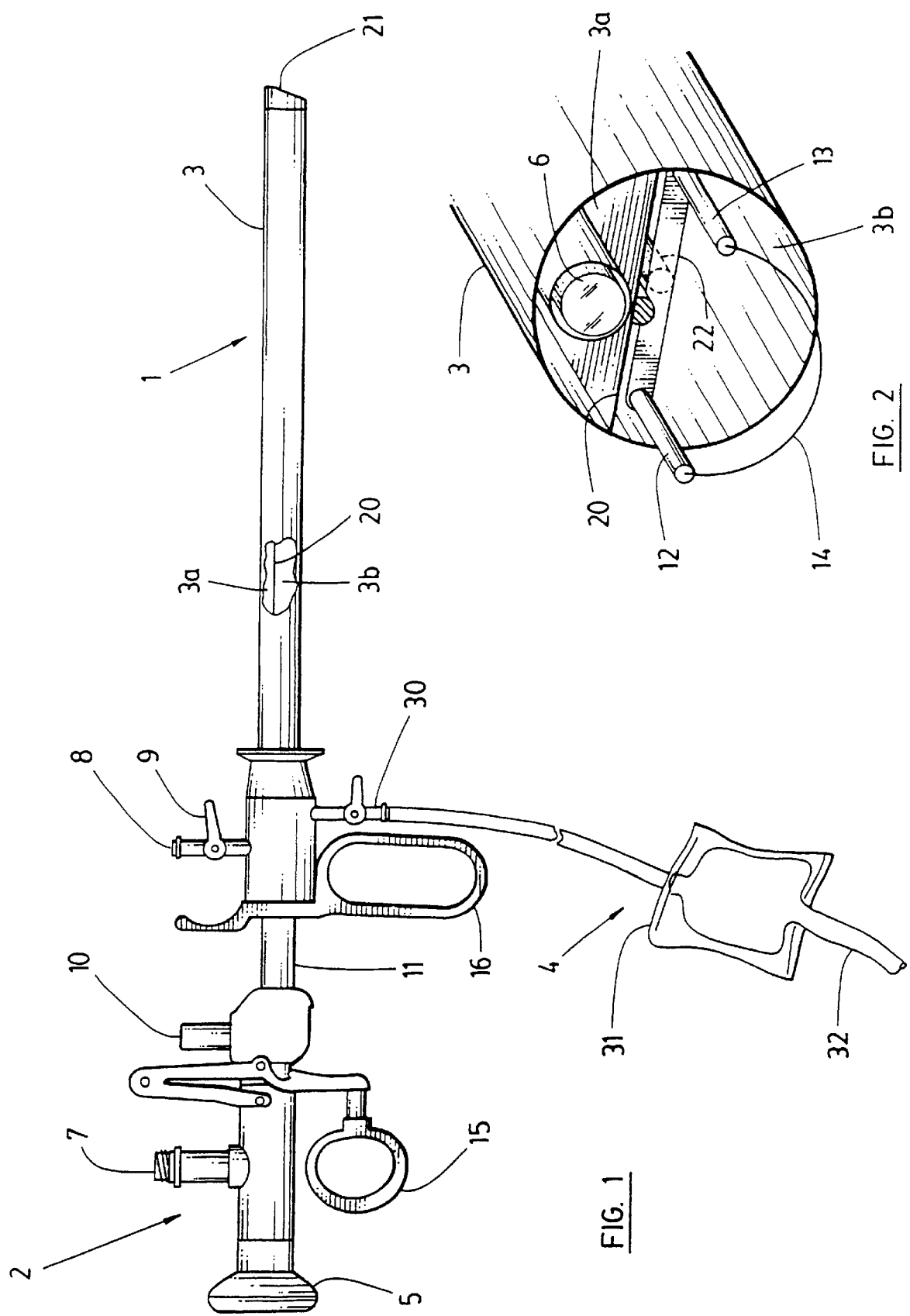

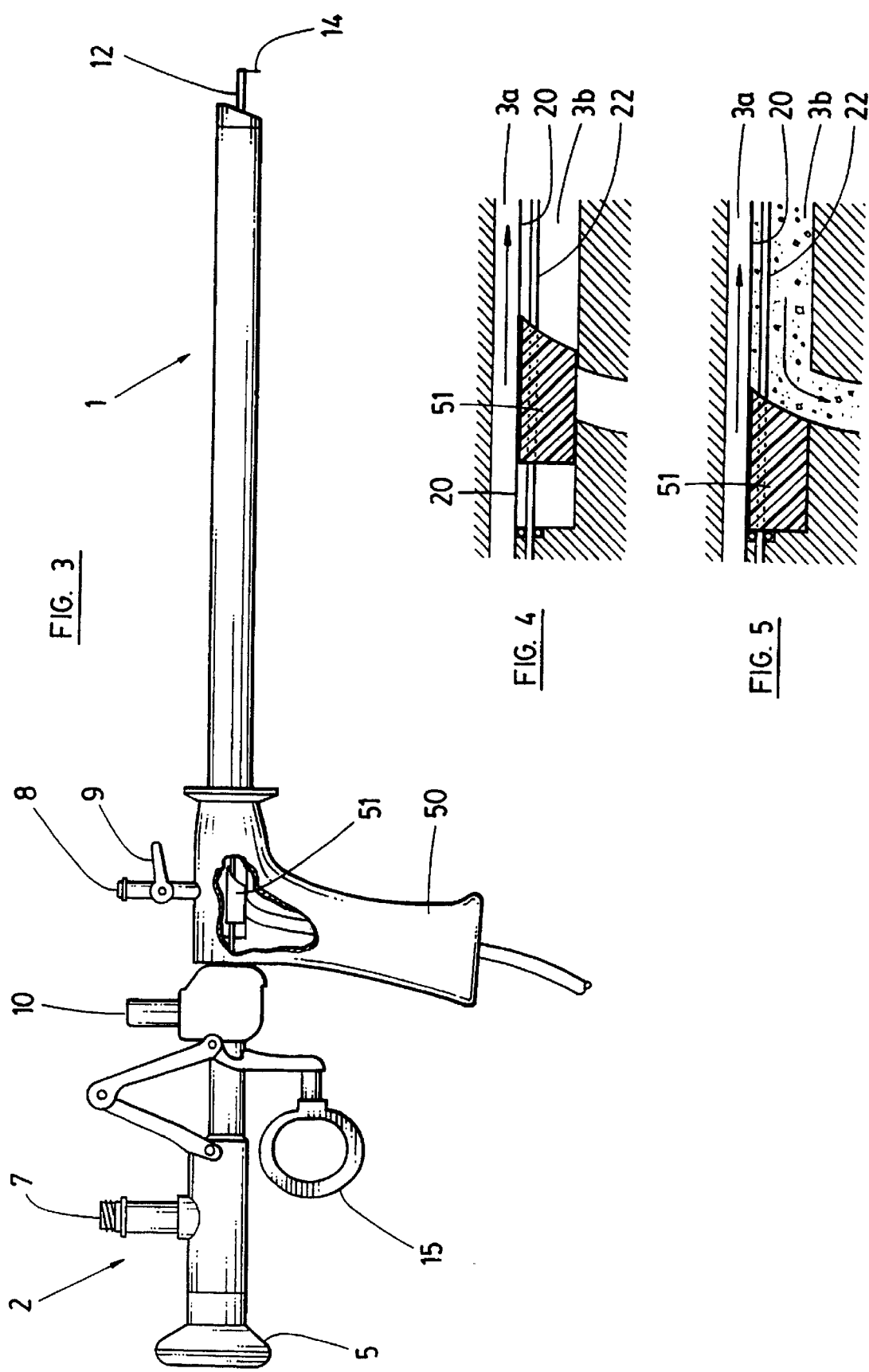

DEBRIS ASPIRATING RESECTOSCOPE

BACKGROUND OF THE INVENTION

1. Field of Art

This invention relates to the field of surgical equipment for use in the practice of medicine and, in particular, relates to an improved resectoscope.

2. Prior Art

A conventional resectoscope for internal surgery generally comprises an operating handle with two sections that slide forward and backward relative to one another under the control of an operator using finger and thumb grips; various extensions protruding from one or the other of the handle sections (for relative movement) which may include a cutting instrument, a telescope for viewing the site of the surgery, a light conduit to illuminate the site, and a means for providing an aspirating fluid to lubricate and to wash the site, and a pair of coaxial tubes which contain the extendible parts and shield them from the patient except at the distal end of the tubes. The inner tube extending from the handle typically encloses the telescope, light conduit, and cutting instrument. An outer tube or atraumatic meatus stopper surrounds the inner tube. The aspirating fluid may wash the tip of the telescope to maintain clear viewing, distend flesh about the cutting instrument, collect surgical morsels from the cutting instrument, and carry them back through the resectoscope to a collection device where the morsels may be filtered from the fluid. Other attachments are known, for example, a video camera may be connected to the telescope to display the surgical site on a television monitor. The cutting instrument may be one of many known types such as: a cutting loop, a roller ball, a roller bar, or an electrode. Electric circuits may be provided within the resectoscope tubes to power such instruments. Examples of prior art patents disclosing similar devices are discussed below.

U.S. Pat. Nos. 3,835,842, and 3,850,175, relate to endoscopic urological devices that provide a conduit for the inflow of clear irrigating fluid to the operative field, and an outflow conduit for removing turbid fluid from the field using suction. The conduits are formed by providing an inner sheath within an outer sheath.

U.S. Pat. No. 5,176,677 relates to a surgical instrument with a hand piece, a vibration source to effect cutting of tissue, a telescope, and an irrigation system. It discloses the use of an ultrasonic surgical device that provides both irrigation and aspiration as well as tip rotation. An electrocauterizing current is provided in the cutting tip of a cutting instrument. A telescope near the cutting tip permits the surgeon to view the tissue. Irrigation of the site with aspirating fluid is provided through a luer fitting to improve visibility through the telescope and to wash tissue back through a hollow tip into a suitable collection vessel.

U.S. Pat. No. 5,456,689 relates to a tissue resection device in which tissue morsels are removed from the cutter through an aspiration lumen within the shaft. As the aspirated fluid is withdrawn, the morsels from the surgery are trapped and separated from the aspirated fluid by a filter screen. The viewing tube is surrounded by the inflow passageway and the morsels are withdrawn through a tube which supports the cutting instrument.

U.S. Pat. No. 5,201,731 relates to a resectoscope for prostate surgery with a rotating cutting element mounted within an outer tube. In addition to the rotating cutting blade, there is a laser light beam fed through an optic filament to cut and coagulate the resected area. Irrigation is provided to the area between inner and outer tubes and is withdrawn through the inner tube. The surgeon can view the cutting operation through a telescope provided through the cutting element. The chips or morsels of tissue are withdrawn with the irrigation fluid through the inner tube.

U.S. Pat. No. 5,542,929 discloses an aspiration device with side valves for reducing whistling noise when the aspirator is under pressure.

U.S. Pat. No. 5,527,331 relates to a tissue resection device having a rigid tube with second drive tube rotatably located within it and a cutting head mounted on the drive tube. Resection is achieved by either conventional cutting or electrocautery. An optic fibre is used for viewing. The morsels removed by the cutter are extracted immediately through the aspiration lumen in the rotating shaft. A disposable cartridge filters the surgical debris.

Other patents of interest include U.S. Pat. Nos. 5,542,928; 5,542,918; 5,542,917; 5,540,683; 5,540,679; 5,540,678; 5,540,658; 5,540,656; 5,536,234; 5,314,438; 5,313,949; 5,133,713; 5,000,185; and 4,681,106.

There is a limit in the size of a resectoscope which is determined by the comfort of the patient and the manipulation requirements of the surgeon. This size limitation becomes significant when one wishes to remove surgical morsels for testing and further examination. For example, an outer tube, which contains all the various elements that extend into a patient, may be about 8 to 9 mm in outside diameter. An inner tube may be about 7 mm in outside diameter. A standard telescope may be about 3–3.5 mm. The conventional structure of concentric inner and outer tubes provides a passage between them of significant cross-sectional area, but the radial difference between the tubes is small. Without going into further detail, it may be appreciated that the conventional structure limits the free space for passage of aspirating fluid and it may become blocked when the fluid from the surgical site contains clots, coarse debris, and tissue.

SUMMARY OF THE INVENTION

The present invention is directed to a novel structure of a resectoscope to increase the ability to transmit aspirating fluid and surgical debris through the resectoscope. The new structure does not have an inner tube and outer tube, but, rather, one tube divided in cross section by a longitudinally extending wall into a first segment and a second, larger, segment to form passageways for the aspirating fluid and the parts of the resectoscope that extend to the surgical site. The first passageway is sized to carry a telescope and a light conduit and to provide some free space for incoming clear, aspirating fluid. The second passageway occupies the balance of the cross section of the tube for the removal of surgical debris.

More precisely, one embodiment of the invention is a resectoscope for surgery at an internal surgical site comprising:

an operating handle having a first section and a second section, which slide longitudinally in relation to one another to selected positions in a range between a most forward position and a most rearward position;

a tube, extending from the second section of the operating handle, divided in cross section by means of a longitudinally extending wall into first and second segments;

the first segment of the tube containing a viewing means connected to the second section of the operating handle and extending along the length of the first sector of the tube, and providing an open passageway adjacent the viewing means for the supply of aspirating fluid to the surgical site;

the second segment of the tube containing a cutting tool connected by an extension means to the first section of the operating handle, the extension means having a sufficient length to extend the cutting tool to a distal end of the second segment of the tube when the first and second sections are at the most rearward position and to extend the cutting tool beyond the distal end at the most forward position of the sections, and providing a passageway for removal of aspirating fluid and surgical morsels.

In another embodiment described hereafter the second passageway has a valve mechanism to control the flow of outgoing aspirating fluid and surgical debris.

BRIEF DESCRIPTION OF THE DRAWING FIGURES

The invention is more fully described in connection with the attached drawings wherein:

FIG. 1 is a side view of a first embodiment of the resectoscope of this invention having an externally mounted valve system;

FIG. 2 is a perspective view of the distal end of the improved resectoscope showing the novel first and second passageways of the covering tube;

FIG. 3 is a side view of a second embodiment of the resectoscope of this invention having a second passageway valve, which is shown in the valve closed position;

FIG. 4 is a side view of the apparatus of FIG. 3 in the valve closed position; and FIG. 5 is a side view of the apparatus of FIG. 3 in the valve open position.

DETAILED DESCRIPTION OF THE PREFERRED EMBODIMENTS

The first embodiment of the improved resectoscope 1 of this invention is shown in FIGS. 1 and 2. It comprises a handle mechanism generally indicated as 2, a tube 3, and a surgical debris collection mechanism 4. The handle mechanism 2 includes an eyepiece 5 for a telescope 6 (see FIG. 2) which extends through the tube 3 to project from the distal end of the tube 3. A light conduit (not shown) may be provided through an opening 7 in the handle 2 to lie alongside the telescope 6 to light the surgical area. Aspirating fluid (not shown) may be introduced through an inflow pipe 8 having a luerlock valve 9, which controls the flow rate of the aspirating fluid entering the resectoscope tube 3. An electrical cable (not shown), may be led into receptacle 10 to provide electric current to an electrode 11 which extends along the tube 3 and connects insulators 12 and 13, to power a cutting loop 14 or similar surgical device (see FIG. 2). The handle 2 has hand grips 15 and 16 which enable the surgeon to insert and withdraw the cutting loop through the tube 3 as required from time to time during surgery.

FIG. 2 best illustrates the novel construction of the tube 3. The tube 3 is divided into two segments in cross section by a partition wall 20, forming a first passageway 3a and a second passageway 3b. The first passageway 3a is sized to envelop the telescope 6 near the top of the tube 3 and to provide sufficient space for introduction of a light conduit (not shown) beside the telescope 6 and for an inflow of aspirating fluid to the surgical site along each side of the telescope 6. Thus the fluid leaving the passageway 3a washes over the telescope 6 and the light conduit to keep them clean during surgery. The aspirating fluid also distends the flesh surrounding the tip 21 at the end of the tube 3 (see FIG. 1) and to wash over the cutting loop 14 and to return with surgical debris through the enlarged outflow passageway 3b. The tip 21 may be a ceramic insulating material. The partition 20, cutting off a sector of the area of the tube cross section, provides a much larger dimension for the second passageway 3b than is provided by the prior art concentric tubes. Thus, the second passageway 3b permits clots and large morsels to pass through the resectoscope 1 for collection.

As illustrated in FIG. 1, the outflow passageway 3b is connected to conduit 30 in handle portion 2 which carries the aspirating fluid and surgical debris to a filter bag 31 where the surgical morsels are collected and the aspirating fluid is allowed to pass out through the tubing 32 to a suction device (not shown).

Another embodiment with an integral valve mechanism is shown in FIGS. 3–5. FIGS. 3 and 4 illustrate that the second passageway, the outflow passageway 3b, passes along the length of the tube 3 and into the handle mechanism 2 of the resectoscope 1. The front handle grip 50 is hollow to act as a conduit of the aspirating fluid and surgical debris from the outflow passageway 3b to the tubing and the filter bag (not illustrated). In this embodiment a valve 51 is connected to the stabilizer rod 22 so that the conduit of the grip of the handle grip 50 is closed by the valve 51 as the cutting loop 14 is projected outward to the surgical site. The aspirating fluid entering the inflow passageway 3a alongside the telescope 6 is thus pressurized to distend the tissue surrounding the surgical site to clear the path for the cutting loop. As illustrated in FIG. 5, as the hand grip 15 is withdrawn to pull the cutting loop 14 back into the tube 3, the stabilizer rod 22 withdraws the valve 51 from the conduit of a portion of the handle grip 50 to permit the aspirating fluid and surgical debris to be drawn out of the surgical site to a filter bag or other collecting mechanism.

The foregoing description of the preferred embodiments is intended to be illustrative of the novel features of this invention. It will be appreciated by those skilled in the art that one may make obvious departures and substitutions from the said embodiments while retaining the essence of this invention. The true scope of this invention may be determined from reading this specification, including the claims, as a whole in light of the relevant art.

The embodiments of the invention in which an exclusive property or privilege is claimed are defined as follows:

1. A resectoscope for surgery at an internal surgical site comprising:

an operating handle having a first section and a second section that slide longitudinally in relation to one another, and a tube, extending from the second section of the operating handle;

said tube divided in cross section by means of a longitudinally extending wall into a first segment and a larger second segment;

said first segment of the tube containing a viewing means connected to the second section of the operating handle and extending along the length of the first segment of said tube, and providing an open passageway adjacent said viewing means for the supply of aspirating fluid to the surgical site; and said larger second segment of the tube containing a cutting tool and defining a second passageway to allow aspirating fluid and surgical morsels to pass therethrough, wherein said second passageway occupies substantially all of said larger second segment, and said cutting tool is connected by an extension means to said first section of the operating handle, said extension means having a sufficient length to extend the cutting tool to a distal end of the larger second segment of the tube when the first section is at a most rearward position relative to the second section, and to extend the cutting tool beyond said distal end when the first section is at a most forward position relative to the second section.

2. The resectoscope of claim 1 in which the second section has a finger grip and the first section has a thumb grip, said second section fitting within said first section to slide longitudinally in response to the relative movements of the thumb and finger grips as determined by an operator from time to time.

3. The resectoscope of claim 1 in which a collection means to receive aspirating fluid and surgical morsels is connected to an exhaust port from the second segment of the tube.

4. The resectoscope of claim 3 in which a valve is located in said larger second segment and connected to the extension means of the cutting tool to close the exhaust port when the first section is at a most forward position relative to the second section to cause the cutting tool to protrude beyond the distal end of the tube, and to open the exhaust port when the first section is at a most rearward position relative to the second section to cause the cutting tool to retract into the tube.

5. A resectoscope for surgery at an internal surgical site comprising:

an operating handle having a first section and a second section that slide longitudinally in relation to one another;

a tube, extending from the second section of the operating handle, said tube divided in cross section by means of a longitudinally extending wall into a first segment and a second segment;

said first segment of the tube containing a viewing means connected to the second section of the operating handle and extending along the length of the first segment of said tube, and providing an open passageway adjacent said viewing means for the supply of aspirating fluid to the surgical site;

said second segment of the tube containing a cutting tool connected by an extension means to said first section of the operating handle, said extension means having a sufficient length to extend the cutting tool to a distal end of the second segment of the tube when the first section is at a most rearward position relative to the second section, and to extend the cutting tool beyond said distal end when the first section is at a most forward position relative to the second section; and, a valve and an exhaust port both located in said second segment, said valve being connected to the extension means of the cutting tool to close said exhaust port when the first section is at said most forward position, and to open the exhaust port when the first section is at said most rearward position.

6. The resectoscope of claim 5 in which the second section has a finger grip and the first section has a thumb grip, said second section fitting within said first section to slide longitudinally in response to the relative movements of the thumb and finger grips as determined by an operator from time to time.

7. The resectoscope of claim 5 in which a collection means to receive aspirating fluid and surgical morsels is connected to said exhaust port from the second segment of the tube.

8. The resectoscope of claim 5 in which said second segment defines a second passageway, wherein said second segment is larger than said first segment and said second passageway occupies substantially all of said second segment to allow aspirating fluid and surgical morsels to pass therethrough.

* * * * *